United States Patent [19]

Teshima et al.

[11] Patent Number: 4,983,512
[45] Date of Patent: Jan. 8, 1991

[54] REAGENT FOR DETERMINATION OF ACID PHOSPHATASE

[75] Inventors: Shinichi Teshima, Tsuruga; Yuzo Hayashi, Kobe, both of Japan

[73] Assignee: Toyo Boseki Kabushiki Kaisha, Osaka, Japan

[21] Appl. No.: 38,249

[22] Filed: Apr. 14, 1987

[51] Int. Cl.$^5$ .............................................. C12Q 1/42
[52] U.S. Cl. .......................................... 435/21; 435/4
[58] Field of Search ....................... 435/21, 4; 558/193

[56] References Cited

PUBLICATIONS

Faith et al., *Chemical Abstracts*, vol. 70:3538n, No. 1 (1969).
Lorentz et al., *Enzyme*, vol. 20, pp. 248–256 (1975).
Kanejima et al., *Chemical Abstracts*, vol. 107:129964z (1987).
Kirby et al. (1), *Journal of the American Chemical Society*, vol. 89(20, pp. 415–423 (1967).
Kirby et al. (2), *Journal of the Chemical Society*, pp. 135–141 (1968).
de Jongh et al., *RECUEIL*, vol. 87, pp. 1327–1338 (1968).

*Primary Examiner*—Esther L. Kepplinger
*Assistant Examiner*—Janelle Graeter
*Attorney, Agent, or Firm*—Wegner, Cantor, Mueller & Player

[57] ABSTRACT

A reagent for the determination of acid phosphatase in body fluids which contains as a substrate a compound of the formula:

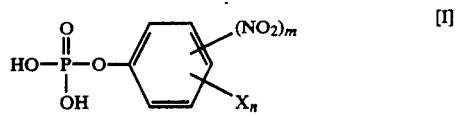

wherein X is a halogen atom, and n and m are each an integer of 1 to 4, and a method for the determination of acid phosphatase in body fluids using the reagent. The reagent is clinically useful for diagnosis of prostate diseases such as prostate carcinoma and prostatomegaly and observation of progress thereof.

2 Claims, 1 Drawing Sheet

REAGENT FOR DETERMINATION OF ACID PHOSPHATASE

This invention relates to a reagent for the determination of acid phosphatase, more particularly to a reagent for the determination of acid phosphatase which contains as a substrate a compound of the formula [I]:

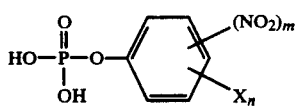

wherein X is a halogen atom, and n and m are each an integer of 1 to 4, which is clinically useful for the diagnosis of prostate diseases and observation of progress thereof.

Prior Art

It is known that in patients suffering from prostate carcinoma or prostatomegaly, the body fluids such as serum and plasma contain increased amount of acid phosphatase, and hence, the determination of the acid phosphatase in body fluids is useful for the diagnosis of these diseases or observation of the progress thereof.

Acid phosphatase has hitherto been determined by using as a substrate a phosphoric acid bound with p-nitrophenol to the hydroxy group thereof, that is, by reacting the substrate with acid phosphatase, and measuring the released p-nitrophenol by colorimetry (cf. Japanese Patent Publication No. 6480/1983), or by an enzyme immunoassay (abbreviated as "EIA") or by a radio immunoassay (abbreviated as "RIA").

However, in colorimetry using p-nitrophenol, the optimum pH of the enzyme reaction of acid phosphatase (about 5.0) is different from the pH for the coloring reaction of p-nitrophenol (not less than pH 9). Hence, the determination of acid phosphatase must be done in separate systems as to the enzyme reaction and the coloring reaction. Accordingly, this method requires a large number of reagents and steps, to which a rate assay can not be applied, while the rate assay is the most suitable for the determination of an enzyme activity.

EIA and RIA require disadvantageously a long period of time for the procedures and require troublesome procedure.

BRIEF SUMMARY OF THE INVENTION

The present inventors have intensively studied these problems in order to develop an improved method for the determination of acid phosphatase which is suitable for the quantitative determination of acid phosphatase and can be done by a rate assay. The present inventors have found that a specific phosphate is suitable as a substrate for the determination of acid phosphatase, and that a reagent containing said specific phosphate as a substrate is useful for the determination of acid phosphatase in body fluids within very short period of time with high accuracy by a rate assay.

An object of the invention is to provide an improved reagent for the determination of acid phosphatase. Another object of the invention is to provide a method for the determination of acid phosphatase with high accuracy and using easy procedures. These and other objects and advantages of the invention will be apparent to those skilled in the art from the following description.

DETAILED DESCRIPTION OF THE INVENTION

Figure 1:
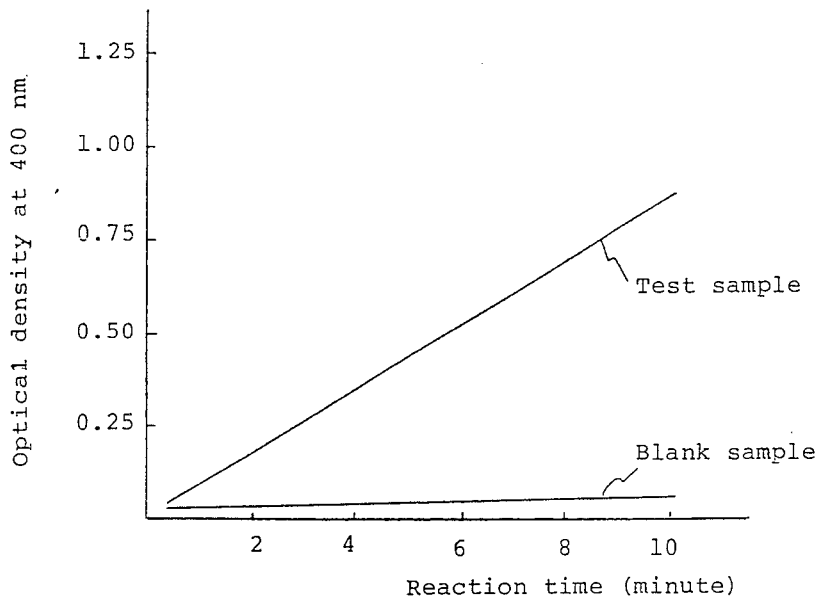
FIG. 1 shows a response graph for the determination of acid phosphatase using a reagent of this invention disclosed in Example 1.

The reagent of this invention contains as a substrate a phosphate compound of the formula [I] as mentioned hereinbefore. In the phosphate compound [I], one of the hydroxy groups of phosphoric acid is bound with a halogen- and nitro-substituted phenyl group. The halogen- and nitro-substituted phenyl group includes a group which can give a phenol compound when cleaved, said phenol compound having an absorption spectrum different from that of the substrate and having the following formula:

wherein X, n and m are as defined above.

Suitable examples of the phenol compound are 2-chloro-4-nitrophenol, 2-bromo-4-nitrophenol, 2-iodo-4-nitrophenol, 2,6-dibromo-4-nitrophenol, 2,6-dichloro-4-nitrophenol, 2,6-diiodo-4-nitrophenol, 2,3,6-trichloro-4-nitrophenol, 2,3,6-tribromo-4-nitrophenol, 2,3,6-triiodo-4-nitrophenol, 2,4-dinitro-6-chlorophenol, 2-fluoro-4-nitrophenol, 2,6-difluoro-4-nitrophenol, 2,3,6-trifluoro-4-nitrophenol, and the like.

The substrate phosphate can be prepared, for example, by reacting a halogen-substituted p-nitrophenol with phosphoryl chloride to give an ester of phosphoric acid (cf. Chemical Abstracts, 47, 8032b), removing the halogen therefrom (cf. Bull. Chem. Soc. Japan, 44, 2743), and then isolating the product in the form of a sodium salt as a crystal (cf. J. Biol. Chem., 167, 57).

The reagent of this invention comprises a solution of the phosphate of the formula [I] in an appropriate buffer. The buffer can include any buffer which has a pH 3.0–6.5 which is the optimum pH of acid phosphatase in body fluids, for example citrate buffer, acetate buffer, succinate buffer, phthalate buffer, and any other organic acid buffers.

The substrate phosphate may be contained in any concentration, but preferably in a concentration at which the acid phosphatase can exhibit the maximum enzymatic activity, for instance, 0.5 mM or more. Usually, the phosphate is contained in a concentration of 0.5 to 3 mM.

The reagent of this invention may also contain other conventional additives, such as surfactants, preservatives, sodium chloride, cyclodextrin, stabilizers, crown ether, and the like.

The determination of acid phosphatase in body fluids such as serum, plasma, urine, etc. can be carried out by using the reagent of this invention in the following manner.

The reagent is added to a test sample containing acid phosphatase to be determined and the mixture is reacted at an appropriate temperature (e.g. 20°–40° C., usually about 37° C.) for 1 to 10 minutes. The change of absorption of the phenol compound produced by the reaction is directly measured with a spectrophotometer by a colorimetric technique. The data are compared with a calibration graph which is previously prepared by the test using a standard solution containing a predetermined amount of acid phosphatase, and thereby, the amount of acid phosphatase contained in the test sample can be determined.

According to the method of this invention using the phosphate of the formula [I], the acid phosphatase in body fluids can easily be measured within a very short period of time with high accuracy by a rate assay method. The method of this invention is particularly characteristic in that the enzymatic reaction and the coloring reaction can advantageously proceed in a single reaction system, while the known method using a nitrophenol-bound compound as a substrate must be done in separate reaction systems. By using the reagent of this invention, the acid phosphatase can easily be determined in body fluids, and thereby, prostate diseases such as prostate carcinoma and prostatomegaly can easily be diagnosed.

This invention is illustrated by the following Examples but should not be construed to be limited thereto.

EXAMPLE 1

Activity of acid phosphatase in a test sample was determined by using the following reagent as follows.

1. Reagent

| | |
|---|---|
| 2,6-Dichloro-4-nitrophenylphosphoric acid | 1.0 mM |
| Citrate buffer | 0.1 M |

2. Method

To a test sample (50 μl) containing acid phosphatase was added the above reagent (2 ml), and the mixture was reacted at 37° C. The absorbance of the reaction mixture (optical density) was measured at a wavelength of 400 nm, and the rate of coloring was determined. The data are drawn in a graph as shown in the accompanying FIG. 1. As a reference, a blank sample containing no acid phosphatase was tested likewise. The results are also shown in FIG. 1.

Standard solutions containing predetermined various concentrations of acid phosphatase were subjected to the same procedures as above and the optical density in each standard solution was likewise measured. The calibration graph shown in the accompanying FIG. 2 was drawn accordingly.

Figure 2:
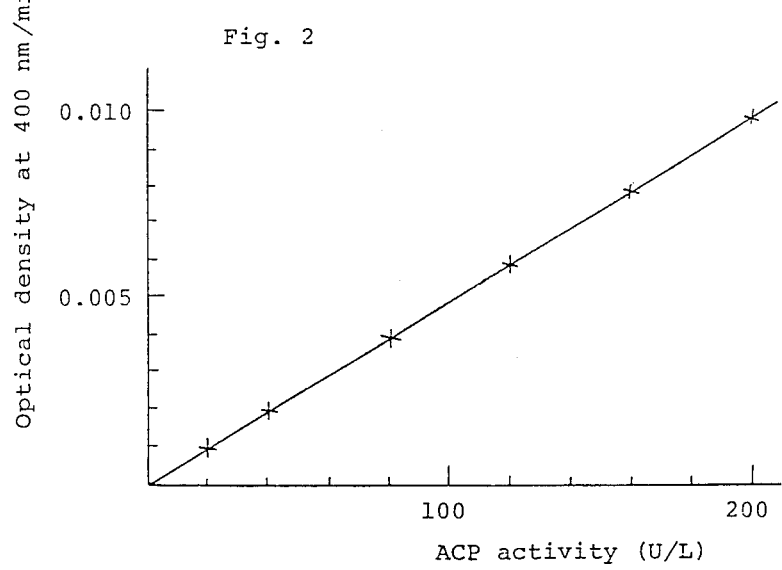
FIG. 2 shows a calibration graph in the determination of acid phosphatase using a reagent of this invention disclosed in Example 1.

As is clear from the comparison of FIG. 1 and FIG. 2, the reagent of this invention using the specific substrate was effective for the determination of acid phosphatase by a rate assay method with high accuracy within a very short period of time and by simple procedures.

EXAMPLE 2

Activity of acid phosphatase in a test sample was determined by using the following reagents as follows.

1. Reagents

| | | |
|---|---|---|
| A. | 2,3,6-Trichloro-4-nitrophenyl-phosphoric acid | 1.0 mM |
| | Citrate buffer | 0.1 M |
| | | pH 4.5 |

| | | |
|---|---|---|
| B. | 4-Nitrophenylphosphoric acid | 1.0 mM |
| | Citrate buffer | 0.1 M |
| | | pH 4.5 |

2. Method (a) To the test sample (50 μl) containing acid phosphatase was added the above reagent A or B (2 ml) and the mixture was reacted at 37° C. for 3 minutes, and then the change of absorbance (optical density) was measured at a wavelength of 400 nm, and the change of the absorbance for one minute was determined. As a blank test, water was used instead of the test sample containing acid phosphatase, and the test was repeated likewise.

(b) To the test sample (50 μl) containing acid phosphatase was added the above reagent A or B (2 ml) and the mixture was reacted at 37° C. for 5 minutes. Thereafter, the reaction mixture was made alkaline by adding thereto a 0.1M aqueous sodium carbonate, by which the reaction was terminated. The absorbance at a wavelength of 400 nm of the reaction mixture was measured. As a blank test, water was used instead of the test sample containing acid phosphatase, and the test was repeated likewise.

The results are shown in Table 1.

TABLE 1

| | Method (a) | | | Method (b) | | |
|---|---|---|---|---|---|---|
| Reagent | Blank | ACP-sample | Data of ACP sample minus data of blank | Blank | ACP-sample | Data of ACP sample minus data of blank |
| A (this invention) | 0.002 | 0.021 | 0.019 | 0.015 | 0.118 | 0.103 |
| B (reference) | 0.000 | 0.000 | 0.000 | 0.013 | 0.121 | 0.108 |

[Note]: ACP-sample means the test sample containing acid phosphatase.

As is clear from the above results, the reagent A of this invention showed sufficient sensitivity for measuring acid phosphatase at pH 4.5, but the reference reagent B did not show any sensitivity at pH 4.5. The reagent B showed the sensitivity only in an alkaline region.

What is claimed is:

1. A method for detecting acid phosphates in body fluids, which comprises reacting a body fluid with a reagent having a substrate compound of the formula:

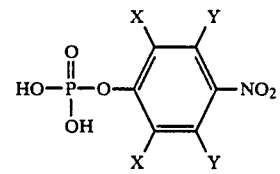

wherein X is a halogen atom, Y is a hydrogen atom or halogen atom, and measuring the absorbance of the released phenol compound by colorimetry.

2. The method according to claim 1, wherein the reagent is a solution of the substrate compound in a buffer having a range of pH 3.0 to 6.5.

* * * * *